United States Patent [19]

Kavadias et al.

[11] Patent Number: 4,575,553
[45] Date of Patent: Mar. 11, 1986

[54] ANTITUMOR M-AMSA ANALOG

[75] Inventors: Gerry Kavadias, Athens, Greece; Terrance W. Doyle, Fayetteville, N.Y.; Elizabeth Janik, Boucherville, Canada; Richard A. Partyka, Liverpool, N.Y.

[73] Assignee: Bristol-Myers Company, New York, N.Y.

[21] Appl. No.: 621,399

[22] Filed: Jun. 18, 1984

[51] Int. Cl.$^4$ .................. A61K 31/47; C07D 219/10
[52] U.S. Cl. ................................. 546/106; 546/103
[58] Field of Search ............... 546/106; 424/257; 514/297

[56] References Cited

FOREIGN PATENT DOCUMENTS 0025705  3/1981  European Pat. Off. .

OTHER PUBLICATIONS

J. Med. Chem. 19, 772, 1124, 1409 (1976).
Drugs of the Future 5, 277 (1980).
Denny, et al., J. Med. Chem. vol. 25, No. 3, pp. 267–315 (1982), pp. 276–278, 281, 284, 298 and 302–315 relied upon and supplied.

Primary Examiner—Donald G. Daus
Assistant Examiner—Diana G. Rivers
Attorney, Agent, or Firm—David M. Morse

[57] ABSTRACT

The compounds are of the class of 9-anilinoacridines, useful as antitumor agents and are analogs of m-AMSA. These compounds have the formula

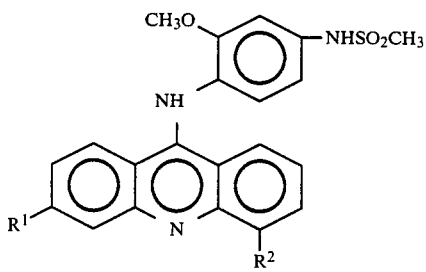

in which $R^1$ is Br, Cl or $CH_3$, and $R^2$ is $CH_2NHCH_3$, $CH_2N(CHO)CH_3$ or $CH_2NHCHO$. Intermediate 3-substituted-9(10H)acridone-5-carboxylic acids are prepared by converting diphenylaminedicarboxylic acids via acyl chloride to dipiperidides, purifying the dipiperidides, treating said dipiperidides with phosphorous oxychloride in an inert organic solvent at a temperature in the range of about 70° C. to 110° C. to yield 9-acridine, subjecting said 9-acridine to mild acid hydroylsis to yield 9-acridone and thereafter hydroylzing said 9-acridones to the acid product.

1 Claim, No Drawings

1

ANTITUMOR M-AMSA ANALOG

BACKGROUND OF THE INVENTION

1. Field of the Invention

The present invention relates to novel analogs of 4'-(9-acridinylamino)-methanesulfon-m-anisidide (m-AMSA), to processes for their production and to their use as anti-tumor agents for the inhibition of malignant tumors in mammals.

2. Description of the Prior Art

The m-AMSA analogs of the present invention in general have the basic structure and numbering system as shown below.

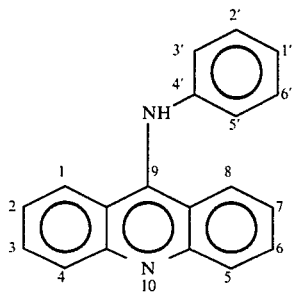

It should be understood that although the numbering system employed is that shown above, some of the prior art uses a reverse system and numbers the acridine nucleus from right to left instead of left to right.

Acridinylaminomethanesulfonanilide derivatives have been studied in recent years for anti-tumor activity. Various examples of both naturally occurring and semi-synthetic compounds of this class have been described in the literature. Illustrative of the more relevant publications are the following:

1. Numerous 4'-(9-acridinylamino)-methanesulfonanilide (AMSA) and 4'-(9-acridinylamino)methanesulfon-m-anisidide (m-AMSA) analogs containing various substituted acridine nuclei are reported to have been investigated for anti-tumor activity in *J. Med. Chem.* 19,772,1124,1409 (1976).

AMSA and m-AMSA have the structural formulae:

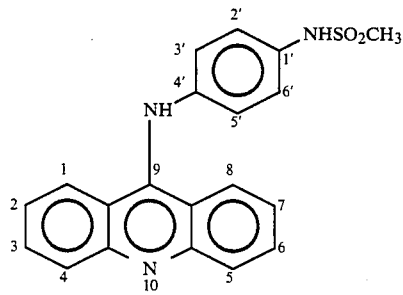

-continued

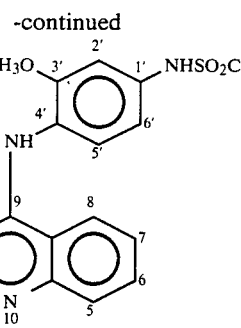

2. It is disclosed in *Drugs of the Future* 5,277 (1980) and references therein that m-AMSA, (1, $R^1=R^2=H$) is a compound with a broad spectrum of experimental anti-tumor activity and has been under clinical evaluation in the treatment of a number of human tumors.

3. European Patent Application No. 0025705A1 discloses m-AMSA analogs having anti-tumor activity in animals of the formula

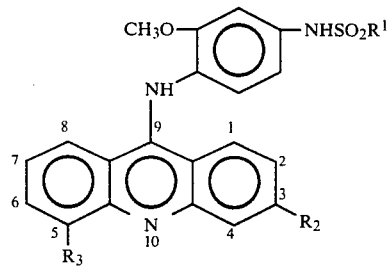

in which:
$R^1$ represents $CH_3$, $CH_2CH_3$, or $(CH_2)_2CH_3$;
$R^2$ represents $CONHR^4$, F, Cl, Br, I, $CF_3$, $NO_2$, $NH_2$, $CH_3$, $OCH_3$, or $NHCOCH_3$; and
$R^3$ represents $CONHR^4$, H, $CH_3$ or $OCH_3$, with the proviso that at least one of $R^2$ and $R^3$ represents $CONHR^4$; and
$R^4$ represents H, $CH_3$, $CH_2CH_3$, $(CH_2)_2CH_3$, $(CH_2)_3CH_3$ or $CH_2CH(CH_3)_2$, each substituted or unsubstituted by one or more of the same of different substituents selected from hydroxyl, amine and amide functions, amine and amide being optionally substituted; and the acid additional salts thereof.

SUMMARY OF THE INVENTION

The present invention provides novel 3,5 disubstituted derivatives of m-AMSA which may be represented by the general formula

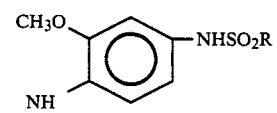
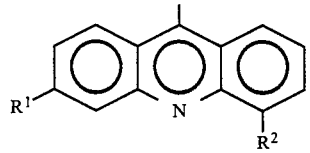

in which
R is $CH_3$,
$R^1$ is Cl, Br, or $CH_3$, and $R^2$ is $CH_2NHCH_3$, $CH_2N(CHO)CH_3$ or $CH_2NHCHO$.

Although the prior art has disclosed a class of m-AMSA analogs containing a carboxamide substituent in the 3 and/or 5 positions in the acridine nucleus which have antitumor activity in animals superior to m-AMSA and low or no direct mutagenicity, the m-AMSA analogs of the present invention now provide surprisingly improved results in comparison to m-AMSA.

The novel compounds of the present invention are prepared by prior art procedures described in the literature. The synthesis of various 3,5-disubstituted m-AMSA analogs requires as intermediates 3-substituted-9(10H)acridone-5-carboxylic acid and their esters. However, the prior art processes for preparation of the 3-substituted-9(10H)acridone-5-carboxylic acids which are employed as starting materials have been less than satisfactory because of the difficulty in separating the isomeric mixtures resulting from such processes. Accordingly, a new process for preparing such compounds involves the cyclization of the dipiperidides with phosphorous oxychloride to 9-chloro-acridines followed by acid hydrolysis.

DETAILED DESCRIPTION

The novel compounds of the present invention may generally be prepared by methods known in the art. Illustrative of such methods are the reaction schemes shown below in schemes 1, 3, 4, 5 and 6. Scheme 2 illustrates the improved method of the present invention for preparing the 3-bromo-, 3-chloro- and 3-methyl-9(10H)acridone-5-carboxylic acids.

SCHEME 1

Preparation of starting materials (prior art) where $R^1$ is Br, Cl or $CH_3$ and $R^2$ is H, $C_2H_5$ or $CH_3$.

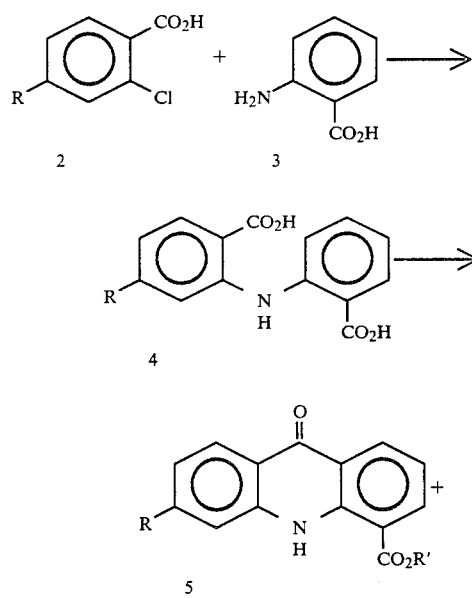

SCHEME 2

Preparation of starting materials where $R^1$ is Cl, Br or $CH_3$ and $R^2$ is H, $C_2H_5$ or $CH_3$.

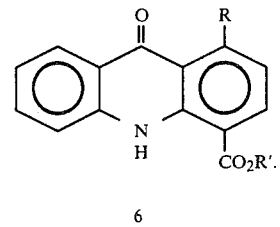

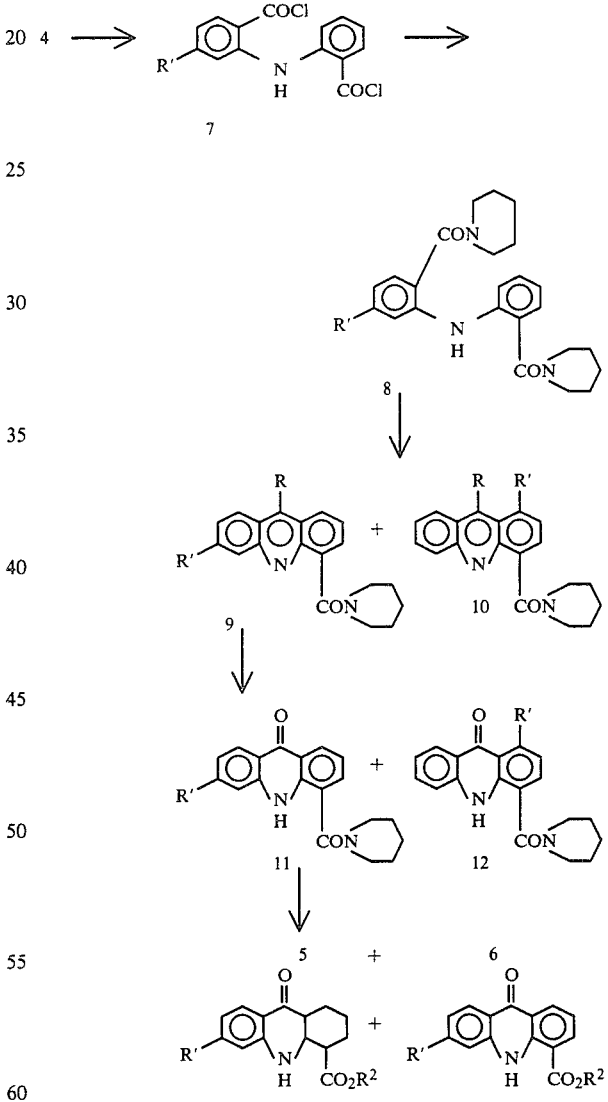

SCHEME 3

Preparation of alkylamino intermediates for the synthesis of 3,5-disubstituted m-AMSA where $R^1$ is Br, Cl or $CH_3$ and $R^2$ is $CH_2NHCH_3$, $CH_2N(CHO)CH_3$ or $CH_2NHCHO$

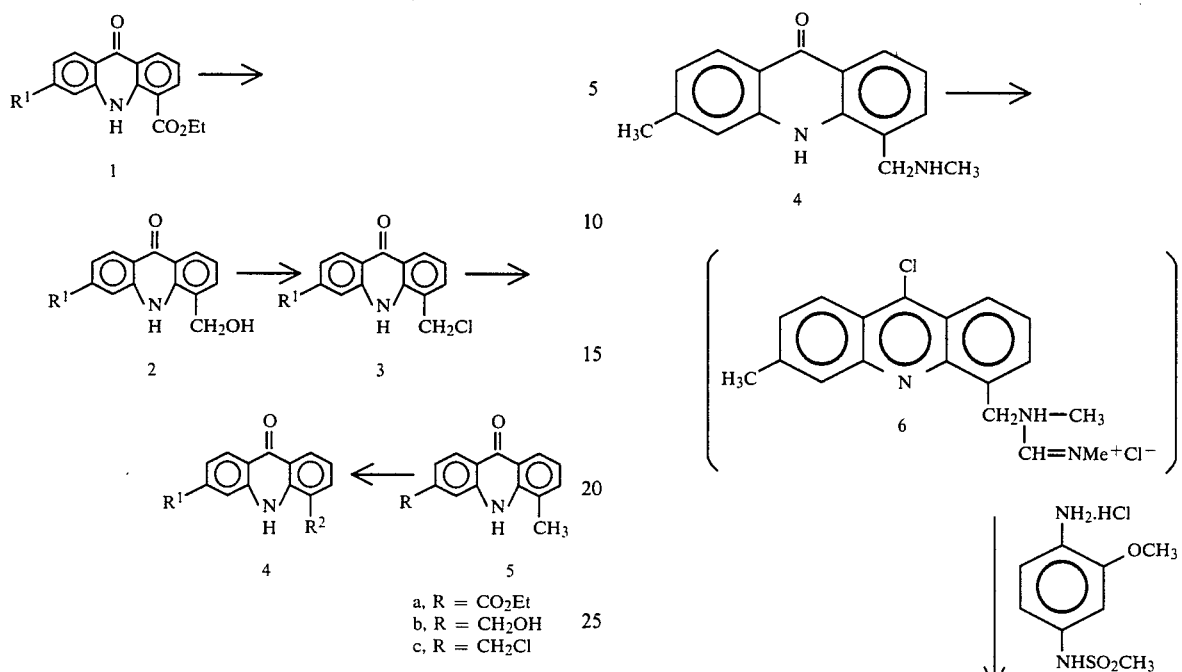
a, R = CO₂Et
b, R = CH₂OH
c, R = CH₂Cl
SCHEME 4
Preparation of formula I where $R^1$ is Br or Cl and $R^2$ is CH₂NHCH₃ or CH₂N(CHO)CH₃
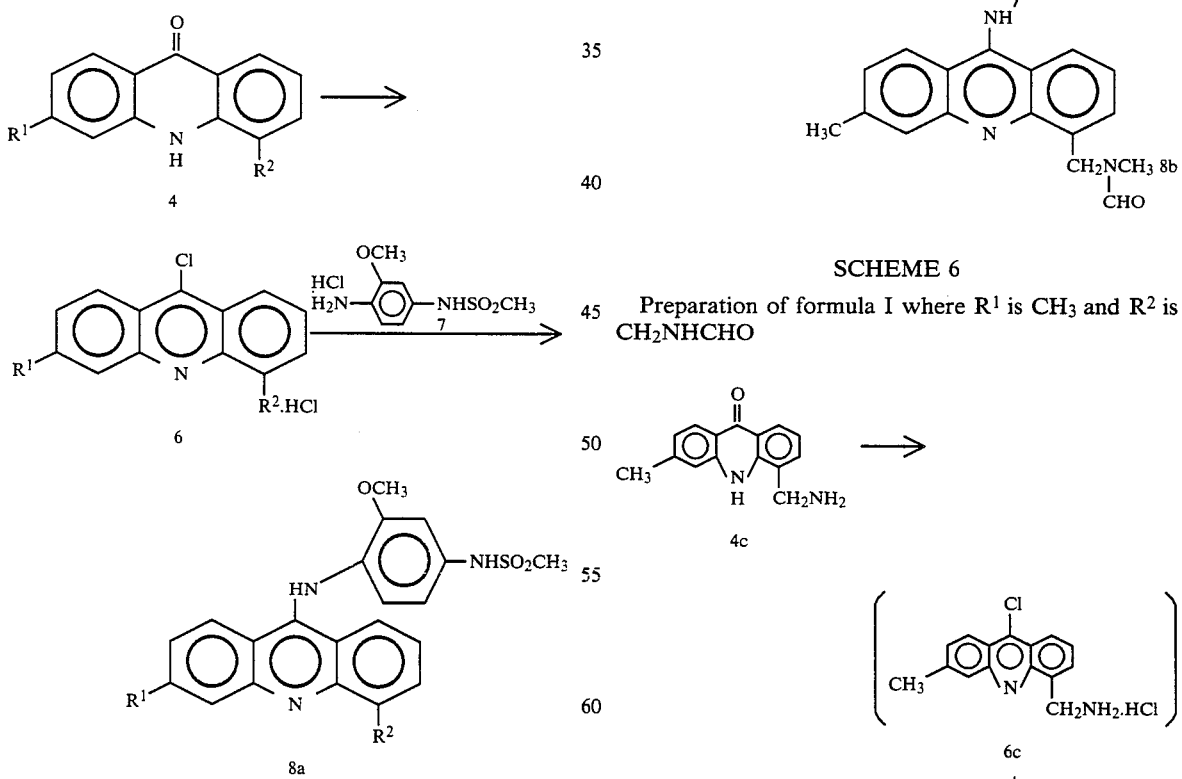
SCHEME 5
Preparation of formula I where $R^1$ is CH₃ and $R^2$ is CH₂N(CHO)CH₃
SCHEME 6
Preparation of formula I where $R^1$ is CH₃ and $R^2$ is CH₂NHCHO

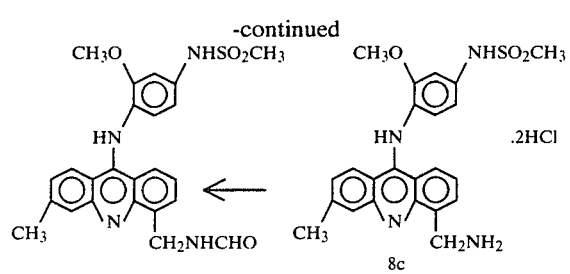

EXPLANATION OF SCHEMES 1-5

Known methodology for the syntheses of the 3-substituted-9(10H)acridone-5-carboxylic acids involves cyclization of the diphenylamine dicarboxylic acids, a general process most often used in the preparation of acridones and their substituted derivatives (Scheme 1). Sulfuric acid, phosphorous oxychloride and dichlorophosphoric acid anhydride are used as the acidic reagents for the cyclization reaction. Cyclization of diphenylamine-dicarboxylic acids yields mixtures or decomposition products which requires difficult separation procedures and in some cases cannot be accomplished by common laboratory techniques. Repeated recrystallizations are inefficacious to provide pure materials mainly because of the low solubilities of both isomers in common organic solvents. Furthermore, the resulting compounds melt above 360° C. and therefore melting points cannot be used as a criterion of their purity.

In order to overcome the deficiencies of the prior art, a new methodology for the synthesis of the intermediate acids was developed (Scheme 2). The new method involves the cyclization of the dipiperidines 8 with phosphorous oxychloride followed by acidic hydrolysis.

Diphenylaminedicarboxylic acids 4 were converted, via the acyl chloride 7, to the dipiperidides 8. Since the purifications of the acids proved to be a difficult task, crude acids were used in these preparations and the products 8 were purified simply by filtration through a silica gel column.

Treatment of the dipiperidides 8 with phosphorous oxychloride affected ring closure and produced predominantly 9-chloroacridines 9 rather than the 9-piperidinoacridines as might have been expected. The ring closure reaction may be carried out in an inert organic solvent such as benzene, toluene, xylene, etc. with heating, preferably at a temperature in the range of from about 70° C. to 110° C. and most preferably at the reflux temperature of the solvent system. Typical was the treatment of N-[2-(2-piperidinocarbonyl)anilino-4-nitrobenzoyl]piperdine with phosphorous oxychloride in benzene at the refluxing temperature and crystallization of the product from 95% ethanol, which gave 3-nitro-9-chloro-5-piperidinocarbonyl-acridine as a crystalline solid. Although isolation and further purification of the resulting compounds is feasible, they have no practical value in the present syntheses and therefore the resulting compounds are prepared and converted to the 9-acridones by mild acid hydrolysis in a single flask. The yields of the 9-acridones thus prepared are influenced by the reaction time in the ring closure step. Optimum yields are afforded when the dipiperidides are treated with phosphorous oxychloride under reflux for 45 minutes; when this period of time is exceeded, the yields are reduced to 60-63% after a period of 3 hours.

Hydrolysis of the 9-acridones is readily accomplished and provided the acids in high yields. Typically, treatment of 3-chloro-5-piperidinocarbonyl-9(10H)acridone with a concentrated hydrochloric acid-acetic acid mixture (1:2) at the refluxing temperature for 24 hours gave 3-chloro-9(10H)acridone-5-carboxylic acid. In an analogous manner, 3-bromo-5-piperidinocarbonyl-9(10H)acridone was hydrolyzed to provide 3-bromo-9(10H)acridone-5-carboxylic acid under the same conditions.

Ethyl and methyl esters were best prepared and in high yields by reaction of the corresponding acid with diethyl and dimethyl sulfate respectively, in the presence of diisopropylethylamine.

Formation of 9-alkylaminoacridines by cyclization of alkylamides of N-phenylanthranilic acid with phosphorous oxychloride is described by E. F. Elslager et al., J.Am.Chem. Soc. 79, 4699 (1957) and others. B. F. Cain et al., J.Med.Chem. 18, 1110 (1975) showed that cyclization of 3-(3-methylanilino)benzopiperidide produced 3-methyl-9-piperidinoacridine, which was readily converted to 3-methyl-9-acridone by mild acid hydrolysis. From the above prior art, it was expected that ring closure of the dipiperidides would proceed in an analogous manner and produce the 9-piperidinoacridines which by hydrolytic cleavage of the piperidine moiety should yield the corresponding 9-acridones. It was surprising to discover that the 9-chloroacridines were the major products of the cyclization of the dipiperidides with phosphorous oxychloride.

The required alkylaminomethyl intermediates for the syntheses of the 3,5-disubstituted m-AMSA where $R^1$ is Br, Cl or $CH_3$ and $R^2$ is $CH_2NHCH_3$, $CH_2N(CHO)CH_3$ or $CH_2NHCHO$ were prepared by the sequence of reactions shown in Scheme 3. The acids: 3-bromo-, 3-chloro- and 3-methyl-9(10H)acridone-5-carboxylic acids were prepared by the procedure of the present invention shown in Scheme 2. The esters were best prepared by reactions of the corresponding acid with diethylsulfate using a modified literature procedure [F. H. Stodola, J. Org. Chem. 29, 2490 (1964)] and were reduced with lithium borohydride to the corresponding alcohols 2. The hydroxymethyl compounds 2 when treated with thionyl chloride produced the 9-chloro-5-chloromethyl analogs which upon mild hydrolysis (95% ethanol) were converted to 3. Amines 4 were prepared from the chloromethyl analogs 3 by treatment with amines.

The preparations of the 3,5-disubstituted m-AMSA of the present invention are shown in Schemes 4, 5 and 6. The 9-chloro-acridines 6 were prepared by reaction of the hydrochloride salts of 4 with thionyl chloride using literature procedures (R. M. Atseson, "The Chemistry of Heterocyclic Compounds" Vol. 9, Interscience Publishers, N.Y. 1956; Cain et al. in all his papers) and were used in the condensation reaction without purification. Condensation of 9-chloroacridines with hydrochloride salts of amines to provide 9-aminoacridines is a known process (R. M. Atseson, "The Chemistry of Heterocyclic Compounds" Vol. 9, Interscience Publishers, N.Y. 1956; Cain et al. in all his papers). 4-Amino-3-methoxymethanesulfonanilide hydrochloride was prepared using a literature procedure [Cain et al., J. Med. Chem. 11, 295 (1968); Cain et al., J. Med. Chem. 18 (11), 1110 (1975)] and was condensed with the 9-chloroacridines 6 to produce the 3,5-disubstituted m-AMSA where $R^1$ is Br, Cl or $CH_3$ and $R^2$ is $CH_2NHCH_3$ or $CH_2N(CHO)CH_3$. It was found that dry dimethyl formamide (DMF) is a superior solvent for the condensation reaction than ethanol or aqueous ethanol which have been previously used for this reaction (Cain et al. in all his publications). In DMF, hydrolysis of 9-chloroacridines to 9-acridones is at a minimum and the products usually precipitate in pure form. Compounds of the present invention as described above were isolated as the dihydrochloride monohydrate salts.

The preparation of the 3,5-disubstituted m-AMSA where $R^1$ is $CH_3$ and $R^2$ is $CH_2N(CHO)CH_3$ is shown in Scheme 5. These products may be prepared by reaction of 3-methyl-5-methyl-aminomethyl-9(10H)acridone, 4, with thionyl chloride and an equimolar quantity of DMF to give the 9-chloro intermediate 6 which upon condensation with 7 provided the N-formyl compound, 8. Substitution of 5-chloromethyl-3-methyl-9(10H)acridone for 3-methyl-5-methylamine-9(10H)acridone is shown in Scheme 6 and yields a 3,5-disubstituted m-AMSA where $R^1$ is $CH_3$ and $R^2$ is $CH_2NHCHO$.

BIOLOGICAL ACTIVITY

Representative compounds of the present invention were tested for antitumor activity against transplantable mouse tumors B16 melanoma, Madison 109 lung carcinoma, L-1210 leukemia, and the results of these tests are shown below in Tables I–IV. The methodology used generally followed the protocols of the National Cancer Institute [see, for example, Cancer Chemotherapy Rep. Part 3, 3:1–103 (1972)]. The essential experimental details are given at the bottom of the tables.

TABLE I
Effect of Compound of Example I on L1210 Leukemia

| Material | Dose, IP mg/kg | MST Days | Effect MST % T/C | Average Weight Change g d.5 | Survivors Day 5 (30) |
|---|---|---|---|---|---|
| m-AMSA | 32 | TOX | TOX | TOX | 2/6 |
|  | 24 | TOX | TOX | −3.3 | 3/6 |
|  | 18 | 11.0 | 157 | −1.6 | 6/6 |
|  | 12 | 9.5 | 136 | −0.6 | 6/6 |
| Compound of Example I | 128 | TOX | TOX | TOX | 0/6 |
|  | 96 | TOX | TOX | TOX | 1/6 |
|  | 64 | TOX | TOX | −4.2 | 3/6 |
|  | 32 | 9.0 | 129 | −2.0 | 6/6 |
|  | 16 | 16.5 | 236 | −0.5 | 6/6 |
|  | 2 | 11.0 | 157 | −0.3 | 6/6 |
| Control | Saline | 7.0 | — | +3.2 | 10/10 |

Tumor inoculum: $10^6$ ascites cells implanted i.p.
Host: CDF mice.
Treatment: Day 1 only.
TOX: <4/6 mice alive on Day 5.
Evaluation: MST = median survival time.
Effect: % T/C = (MST treated/MST control) × 100.
Criteria: % T/C ≧ 125 considered significant antitumor activity.

TABLE II
Effect of Compound of Example II on L1210 Leukemia

| Material | Dose, IP mg/kg/inj | MST Days | Effect MST % T/C | Average Weight Change g d.5 | Survivors Day 5 (30) |
|---|---|---|---|---|---|
| m-AMSA 5% dextrose/water | 32 | 12.0 | 200 | −3.8 | 6/6 |
|  | 24 | 12.5 | 208 | −2.7 | 6/6 |
|  | 18 | 12.0 | 200 | −0.7 | 6/6 |
|  | 12 | 11.5 | 192 | −0.4 | 6/6 |
| Compound of Example II (in sterile, distilled water) | 128 | TOX | TOX | TOX | 0/6 |
|  | 96 | 12.0 | 200 | −4.8 | 4/6 |
|  | 64 | 17.0 | 283 | −3.4 | 5/6 |
|  | 32 | 15.0 | 250 | −2.1 | 5/5 |
|  | 16 | 12.0 | 200 | −0.6 | 6/6 |
|  | 8 | 11.0 | 183 | −1.2 | 6/6 |
| Control | Saline | 6.0 | — | +1.4 | 9/9 |

Tumor inoculum: $10^6$ ascites cells implanted i.p.
Host: $CDF_1$ mice.
TOX: <4/6 mice alive on Day 5.
Treatment: Day 1 only.
Evaluation: MST = median survival time.
Effect: % T/C = (MST treated/MST control) × 100.
Criteria: % T/C ≧ 125 considered significant antitumor activity.

TABLE III
Effect of Compounds of Examples I and II on B16 Melanoma

| Material | Treatment Schedule | Dose, IP mg/kg/inj | MST Days | Effect MST % T/C | Average Weight Change g d.5 | Survivors d.10 (cures d.60) |
|---|---|---|---|---|---|---|
| AMSA 5% D/W | qd 1 → 9 | 4 | >60.0 | >250[a] | −1.6 | 10/10 (7) |
|  |  | 2 | 48.5 | 202[b] | −2.4 | 10/10 (2) |
|  |  | 1 | 36.0 | 150 | −2.0 | 10/10 |
|  |  | 0.5 | 30.5 | 127 | −2.6 | 10/10 |
|  | d.1, 5 & 9 | 12 | 59.0 | 246 | −2.2 | 7/10 (3) |
|  |  | 8 | >60.0 | >250[a] | −2.6 | 7/10 (7) |
|  |  | 4 | 47.0 | 196 | −1.8 | 10/10 |
| Compound of Example I (in sterile, distilled water) | qd 1 → 9 | 4 | TOX | TOX | −3.3 | 2/10 |
|  |  | 3 | 13.5 | 56 | −2.7 | 10/10 |
|  |  | 2 | 51.0 | 213[c] | −2.7 | 10/10 (4) |
|  |  | 1 | 45.0 | 188 | −2.2 | 9/9 (2) |
| Compound of Example II (in sterile, distilled water) | qd 1 → 9 | 8 | 26.0 | 108 | −2.7 | 9/10 (3) |
|  |  | 6 | >60.0 | >250[d] | −2.7 | 9/10 (7) |
|  |  | 4 | >60.0 | >250[e] | −2.6 | 9/10 (6) |
|  |  | 2 | 50.0 | 210[f] | −1.9 | 10/10 (3) |

TABLE III-continued

Effect of Compounds of Examples I and II on B16 Melanoma

| Material | Treatment Schedule | Dose, IP mg/kg/inj | MST Days | Effect MST % T/C | Average Weight Change g d.5 | Survivors d.10 (cures d.60) |
|---|---|---|---|---|---|---|
| Control | | Saline | 24.0 | — | −1.6 | 10/10 |

[a] $LD_{10}$ dose levels
[b] $\cdot f$ MST (% T/C) d.m.o. = (b) 46.5 (194%); (c) 34.0 (142%); (d) 54.5 (227%); (e) 34.0 (142%); (f) 45.0 (188%).
Tumor inoculum: $10^6$ ascites cells implanted i.p.
Host: $BDF_1$ mice.
TOX: <7/10 mice alive on d.10.
Evaluation: MST = median survival time.
Effect: % T/C = (MST treated/MST control) × 100.
Criteria: % T/C ≧ 125 considered significant antitumor activity.

TABLE IV

Effect of Compounds of Examples I and II on M109 Carcinoma

| Material(s) Vehicle | Tumor/Expt. #: M109 #127 Treatment Mg/Kg/Dose or Dilution | Rte. Schedule | Med. S.T. | % T/C | Average Weight Change g d.5 | No. Mice Alive/Total d.10 (60) |
|---|---|---|---|---|---|---|
| Implant Level and Site: | 0.5 ML | 2% BREI, IP | | | | |
| Control | | | 15.0 | 100 | −0.1 | 8/8 |
| AMSA | 18 | IP, Q03DX2; 1 | TOX | TOX | −4.2 | 4/8 |
| 5% Dextrose | 12 | | 22.0 | 147 | −2.8 | 7/8 |
| | 8 | | 20.0 | 133 | −1.9 | 8/8 |
| Compound of | 12 | IP, Q03DX2; 1 | 26.0 | 173 | −2.5 | 7/8 (1) A |
| Example I | 8 | | 43.0 | 287 | −2.1 | 7/8 (3) A |
| (in sterile, distilled water) | 4 | | 27.0 | 180 | −1.8 | 8/8 |
| Compound of | 24 | IP, Q03DX2; 1 | 27.0 | 180 | −2.2 | 7/7 |
| Example II | 16 | | 23.0 | 153 | −2.0 | 8/8 |
| (in sterile, distilled water) | 10 | | 37.0 | 247 | −1.3 | 8/8 |
| Implant Level and Site: | 0.5 ML | 0.2% BREI, IP | | | | |
| Control | | | 19.0 | 127 | −0.2 | 7/8 |
| Implant Level and Site: | 0.1 ML | 2% BREI, SC | | | | |
| Control | | | 36.5 | 100 | 0.1 | 8/8 |
| AMSA | 18 | IP, Q03DX2; 1 | TOX | TOX | −3.8 | 4/8 (1) A |
| 5% Dextrose | 12 | | 41.5 | 114 | −3.0 | 8/8 (1) A |
| | 8 | | 40.0 | 110 | −1.4 | 8/8 |
| BC3687 | 12 | IP, Q03DX2; 1 | TOX | TOX | −3.1 | 5/8 |
| H2O | 8 | | 39.0 | 107 | −2.3 | 8/8 |
| | 4 | | 39.5 | 108 | −2.1 | 8/8 |

The experimental animal tests described above demonstrate that the compounds of the present invention possess marked inhibitory action against mammalian malignant tumors.

According to another aspect of this invention, therefore, there is provided a method for therapeutically treating a mammalian host affected by a malignant tumor which comprises administering to said host an effective tumor-inhibiting dose of a compound of the present invention.

In yet another aspect of the invention, a pharmaceutical composition is provided which comprises an effective tumor-inhibiting amount of a compound of formula of the present invention in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred dosages of the compounds of the present invention will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided and the above-mentioned guidelines.

The following examples are not limiting but are intended to be illustrative of this invention.

PREPARATION OF STARTING MATERIALS

Preparation 1

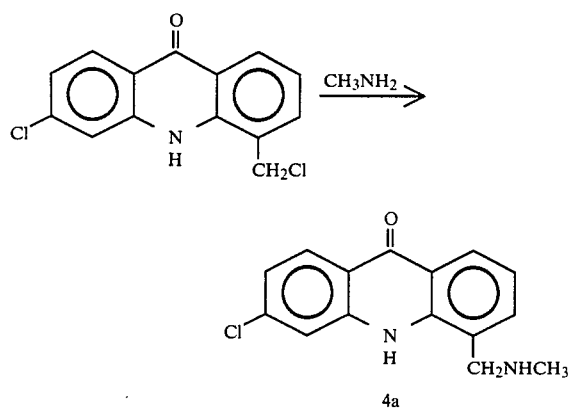

To a solution of methylamine (1.0 g, 32 mmol) in DMF (10 mL) was added 3-chloro-5-chloromethyl-9(10H)acridone (1 g, 3.6 mmol) and the resulting solution was stirred at room temperature for 5 h. The precipitate was collected, washed with ether and dried to give 0.522 g (55.6%) of the title compound, mp 193°–195° C. This product showed on tlc (silica, 5% MeOH—CH₂Cl₂) a single spot of Rf 0.15. From the mother liquor, after evaporation and crystallization of the residue from ethanol, 0.175 g of the compound was obtained increasing the yield to 74.3%.

Anal. calcd. for $C_{15}H_{13}N_2ClO$: C 66.06, H 4.80, N 10.27, Cl 13.00. Found: C 65.37, H 4.83, N 10.23, Cl 12.76.

Preparation 2

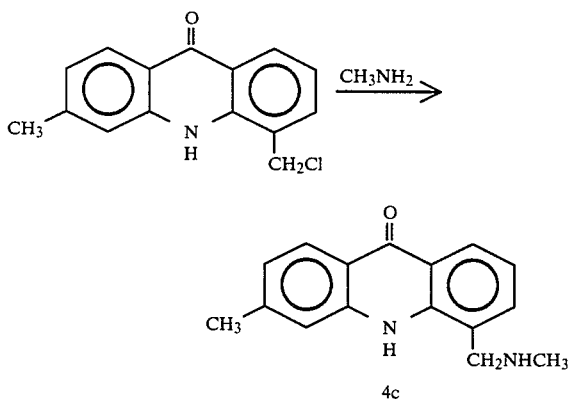

To a solution of methylamine (1 g, 32 mmol) in dry dimethylformamide (10 mL) was added 5-chloromethyl-3 methyl-9(10H)-acridone (443 mg, 1.72 mmol) and the resulting solution was stirred at room temperature for 24 h. The reaction mixture was diluted with methylene chloride and the solution was washed first with 10% sodium bicarbonate and then with water and dried. Removal of the solvent in vacuo gave a residue which was chromatographed on a silica column using first chloroform, then 1% methanol in chloroform and finally 3% methanol in chloroform as eluent. The fractions containing the product were combined and evaporated to give 298 mg (68.7% yield) of product 4C. An analytical sample was obtained by recrystallization from chloroform-ether mixture, mp 154°–157° C.

Anal. calcd. for $C_{16}H_{16}N_2O$: C 76.16, H 6.39; N 11.10. Found: C 75.24, H 6.39, N 10.89.

Preparation 3

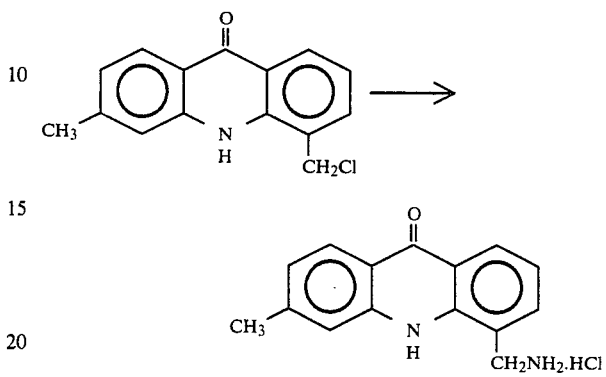

To a solution of DMF (5 ml. saturated with ammonia) was added 5-chloromethyl-3-methyl-9(10H)acridone (0.45 g, 1.75 mmol) and stirred at room temperature for 24 hours. The reaction mixture was diluted with methylene chloride and the solution was washed with 10% sodium bicarbonate and water and dried. After removal of the solvent in vacuo, the residue was chromatographed on a silica gel column using first chloroform, then 1% methanol in chloroform.

EXAMPLE I

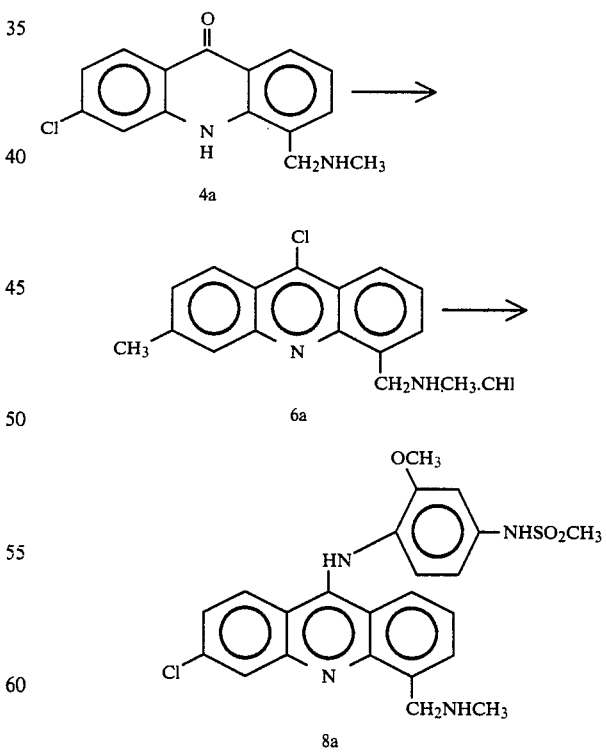

The hydrochloride salt of 4a was obtained by bubbling HCl (gas) into a suspension of 4a (1.0 g, 3.83 mmol) in ethanol and subsequent removal of the solvent in vacuo. The salt, 4a, was then refluxed with SOCl₂ (20 mL) in the presence of DMF (2 drops) for 30 minutes.

The solvent was evaporated and then co-evaporated with benzene to remove any traces of SOCl$_2$ to afford the 9-chloro analog 6a. To a solution of 6a in dry DMF (20 mL) was added 4-amino-3-methoxymethanesulfonanilide hydrochloride (1.16 g, 4.6 mmol) and the mixture heated in an oil bath at 90° with stirring for 1 h. A solid product separated during heating. The solids were collected, washed with ethanol, then ether to give 960 mg (46%) of the dihydrochloride salt of 8a, mp 280° C. (dec.).

$^1$Hmr (DMSO-d$_6$) δ: 2.64 (s, 3H, NCH$_3$), 3.11 (s, 3H, SO$_2$CH$_3$), 3.53 (s, 3H, OCH$_3$), 4.94 (s, 2H, CH$_2$N), 6.92–8.37 (m, 9H, ArH).

Anal. calcd. for C$_{23}$H$_{23}$N$_4$ClO$_3$S.2HCl: C 50.79, H 4.63, N 10.30, Cl 19.56, S 5.89. Found: C 50.50, H 4.69, N 10.72, Cl 19.78, S 5.67.

EXAMPLE II

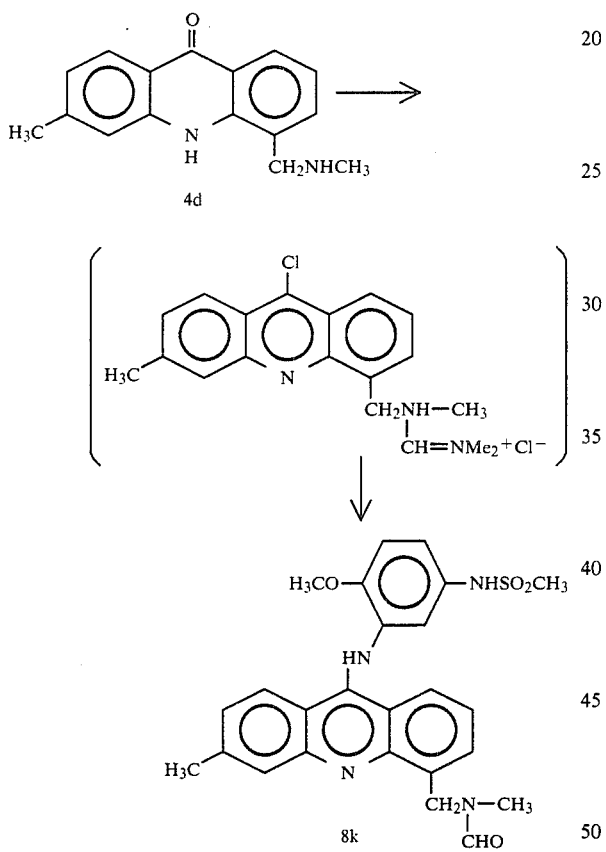

This product was prepared according to the procedure given for Example I using the hydrochloride salt of preparation 1, however, an equimolar amount of DMF was added instead of a catalytic quantity. Thus, the hydrochloride salt of preparation 2 (1.155 g, 4 mmol) suspended in CHCl$_3$ (40 mL) was reacted with thionyl chloride (8 mL) and DMF (0.32 mL, 0.12 mmol) as catalyst. The resulting 9-chloro analog was condensed with 4-amino-3-methoxymethanesulfonanilide (7) (1.06 g, 4.2 mmol) in dry DMF (15 mL). The reaction mixture was diluted with 7% NaHCO$_3$, poured into water (200 mL) and then extracted with CH$_2$Cl$_2$ (3×80 mL). The organic phase was dried (Na$_2$SO$_4$), evaporated and the residue was chromatographed on a dry silica gel column using CHCl$_3$—EtOAc—MeOH (1:1:0.1) as the eluent to afford 1.4 g (63%) of 8k. This product showed on tlc (silica, 20% MeOH—CH$_2$Cl$_2$) a major spot at Rf=0.64. This material was dissolved in CH$_2$Cl$_2$, treated with hydrogen chloride and the solvent was removed to provide the dihydrochloride salt of 8k, mp 232° C. (amorphous mass).

$^1$Hmr (DMSO-d$_6$) δ: 2.53 (s, 3H, C—CH$_3$), 3.02 (s, 3H, NCH$_3$), 3.13 (s, 3H, SO$_2$CH$_3$), 3.56 (s, 3H, OCH$_3$), 4.99 (s, 2H, CH$_2$N), 6.96–8.50 (m, 9H, ArH), 10.11 (bs, 1H, NH), 12.92 (s, 1H, CHO). IR (CHCl$_3$): 1650 (CO) cm$^{-1}$.

Anal. calcd. for C$_{25}$H$_{26}$N$_4$O$_4$S.2HCl: C 54.44, H 5.12, N 10.16, S 5.81. Found: C 54.73, H 5.36, N 10.06, S 6.01.

EXAMPLE III

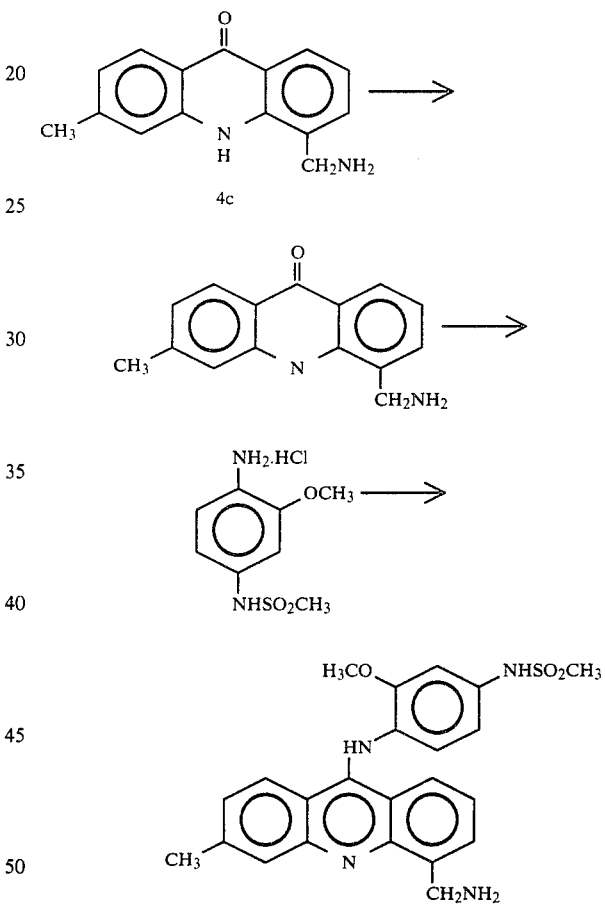

This product may be prepared according to the procedure given for Example I using the hydrochloride salt of preparation 3. Thus the hydrochloride salt of preparation 3 (2 g, 3.9 mmol) suspended in CHCl$_3$ (40 mL) may be reacted with thionyl chloride (8 mL) and DMF (0.32 mL, 0.12 mmol) as a catalyst. The resulting 9-chloro analog may be treated after dissolution in an appropriate solvent (e.g., THF at −20° C.) and then treated with acetic formic anhydride complex according to the procedure of Tet. Lett. 23: 3315 (1982) to give the desired product.

What is claimed is:

1. A compound having the formula

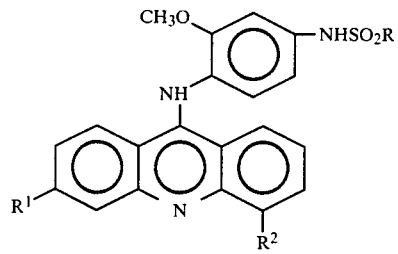
in which
R is CH₃,
R¹ is Cl,
R² is CH₂NHCH₃.
* * * * *